(12) United States Patent
Datta et al.

(10) Patent No.: US 8,475,423 B2
(45) Date of Patent: Jul. 2, 2013

(54) ABSORBENT GARMENT CHARACTERISTICS FOR DROOP ELIMINATION

(75) Inventors: Paul Joseph Datta, Appleton, WI (US); Catherine Marguerite Hancock-Cooke, Neenah, WI (US)

(73) Assignee: Kimberly-Clark Worldwide, inc., Neenah, WI (US)

( * ) Notice: Subject to any disclaimer, the term of this patent is extended or adjusted under 35 U.S.C. 154(b) by 1204 days.

(21) Appl. No.: 10/837,251

(22) Filed: Apr. 30, 2004

(65) Prior Publication Data

US 2005/0256493 A1 Nov. 17, 2005

(51) Int. Cl.
*A61F 13/49* (2006.01)
*A61F 13/62* (2006.01)

(52) U.S. Cl.
USPC .............. 604/385.01; 604/385.3; 604/391

(58) Field of Classification Search
USPC ............... 604/358, 368, 378, 385.01, 385.03, 604/385.25, 385.29
See application file for complete search history.

(56) References Cited

U.S. PATENT DOCUMENTS

| | | | |
|---|---|---|---|
| 5,360,420 A | | 11/1994 | Cook et al. |
| H1674 H | * | 8/1997 | Ames et al. .................. 604/389 |
| 5,858,515 A | | 1/1999 | Stokes et al. |
| 5,876,394 A | * | 3/1999 | Rosch et al. .................. 604/393 |
| 5,931,825 A | * | 8/1999 | Kuen et al. ............... 604/385.08 |
| 7,785,307 B2 | * | 8/2010 | Wennerback ............ 604/385.01 |
| 2002/0032427 A1 | * | 3/2002 | Schmitz et al. ........... 604/385.11 |
| 2002/0040214 A1 | * | 4/2002 | Holmquist ............... 604/385.01 |
| 2002/0165517 A1 | * | 11/2002 | Datta et al. ............... 604/385.22 |
| 2002/0165518 A1 | * | 11/2002 | Datta et al. ............... 604/385.29 |
| 2002/0177829 A1 | | 11/2002 | Fell et al. |
| 2002/0183712 A1 | * | 12/2002 | Datta et al. ............... 604/385.22 |
| 2003/0181883 A1 | | 9/2003 | Olson et al. |
| 2005/0256493 A1 | | 11/2005 | Datta et al. |

FOREIGN PATENT DOCUMENTS

WO   WO 95/14453     6/1995
WO   WO 02/32361 A2  4/2002

OTHER PUBLICATIONS

Search report for WO 2005/110313 A1, Nov. 24, 2005, Datta et al., WIPO, A61F 13/15.*

* cited by examiner

*Primary Examiner* — Susan Su
(74) *Attorney, Agent, or Firm* — Dority & Manning, P.A.

(57) ABSTRACT

An absorbent garment, such as a diaper, designed to reduce or eliminate any tendency of the garment to droop when loaded. The absorbent garment includes an absorbent chassis that defines a waist opening and two leg openings. Based on dimensions of the garment, the absorbent chassis suitably has a diaper length ratio of about 0.85 or less, a droop design ratio of about 150 millimeters or less, and/or an absorbent length design ratio of about 280 millimeters or less.

25 Claims, 3 Drawing Sheets

ABSORBENT GARMENT CHARACTERISTICS FOR DROOP ELIMINATION

BACKGROUND OF THE INVENTION

This invention is directed to an absorbent garment that is designed to reduce or eliminate any tendency of the garment to droop when loaded.

Diapers and other absorbent garments are intended to fit a wearer and to stay on the wearer until removed by the wearer or caregiver. While still in place on the wearer, diapers often droop or sag between the legs of the wearer, particularly when the garment is loaded with bodily wastes. This drooping or sagging may be the result of one or more factors.

The proportion of the garment dimensions appears to be a key factor in garment drooping. For example, some diapers are very long and extend from above the wearer's navel through the crotch region and up the wearer's back. These diapers have front and/or back waist regions that are applied above the wearer's natural waistline. When a diaper is loaded, the added weight in the crotch region pulls the garment down. Quite often when a diaper is pulled down by this added weight, the waist region of the garment comes to rest along the wearer's waistline, thereby resulting in a sagging crotch region. At the waistline the garment comes to rest on the natural bond structure of the wearer's hips.

Some diapers have wide crotch regions. While a wide crotch region provides a storage area for bodily wastes, the excess material is also prone to being pulled down by the weight of bodily wastes, thereby resulting in droopiness in the crotch region. More particularly, the legs and thighs compress a wide crotch width to conform to the dimension between the upper thighs when the wearer is in a natural walking or standing position. When the width of the crotch is reduced by the thighs in this manner, a force is applied downward on the waistband thereby lowering the garment on the body, thus resulting in droop.

Absorbent garments typically include elasticized portions around the leg openings and the waist opening. If the waist elastic has insufficient retraction force, the garment may slide down the wearer's torso, often past the wearer's waistline. Thus, the waist elastic may be another factor that contributes to a drooping tendency of an absorbent garment.

From a manufacturing point of view, it is desirable to include as little material as possible in each absorbent garment to generate cost savings in terms of material expenditures. From a consumer's point of view, it is desirable to include as much material as necessary to provide a comfortable fit as well as adequate absorbency and leak resistance. Thus, it is desirable to optimize the amount of material used in such garments by determining the least amount of material necessary to provide sufficient comfort and functionality.

There is thus a need or desire for an absorbent garment that is designed to eliminate or reduce the occurrence of drooping in the crotch region at a reduced product cost.

SUMMARY OF THE INVENTION

In response to the discussed difficulties and problems encountered in the prior art, a new absorbent garment having optimized dimension proportions has been discovered. These optimized dimension proportions result in reduced droopiness or sagging compared to conventional absorbent garments when loaded. The principles of the present invention may be applied to any of a number of personal care product applications, such as diapers, diaper pants, training pants, swimwear, adult incontinence products, and the like.

The absorbent garment of the invention includes an absorbent chassis that defines a waist opening and two leg openings. The longitudinal length of the garment, measured from a front waist edge of the chassis to a back waist edge of the chassis, is proportionally shorter than conventional diapers dependent on the size of the baby or wearer. Thus, the waist regions of the garment are designed to be situated at a wearer's waistline when worn. The proportionality of the longitudinal length can be assessed with respect to an expanded width of the absorbent chassis measured from a distal edge of one tab to a distal edge of an opposite tab along the back waist region of the absorbent chassis, wherein the distal edges of the tabs define transverse distal edges of the back waist region. The longitudinal length of the absorbent chassis divided by the expanded width of the absorbent chassis is referred to as a diaper length ratio (DLR). The absorbent garment suitably has a diaper length ratio of about 0.85 or less, or about 0.8 or less, or between about 0.6 and about 0.8.

The crotch region of the absorbent garment may also be narrower than the crotch region in corresponding conventional absorbent garments. A narrower crotch region also contributes to a reduction in droopiness. The longitudinal length of the absorbent chassis multiplied by the width of the crotch region and divided by the expanded width of the absorbent chassis is referred to as a droop design ratio (DDR). The absorbent garment suitably has a DDR of about 150 millimeters (mm) or less, or between about 120 and about 140 mm.

Absorbent garments typically include an absorbent core positioned between an outer cover and a body side liner. The combined lengths of the absorbent core and the total absorbent chassis, relative to the width of the crotch region and the expanded width of the absorbent chassis, may be another indication of a garment having a relatively short longitudinal length and/or a relatively narrow crotch region. A sum of the longitudinal length of the absorbent chassis and the longitudinal length of the absorbent core, multiplied by the width of the crotch region and divided by the expanded width of the absorbent chassis is referred to as an absorbent length design ratio (ALR). The absorbent garment suitably has an ALR of about 280 mm or less, or between about 220 and about 250 mm.

The narrow crotch region plus the shorter longitudinal length allows a single-point fastening system to maintain sufficient leg/hip fit, thereby keeping the garment suspended on the wearer even under extreme loads of a forced leak test. In forced leak testing, leakage for diapers with the shorter length was not significantly different from the longer or conventional length diapers in the test. Additionally, the reduction in material in this shorter length, narrower crotch region design also results in cost savings.

Since droop is a more significant problem in absorbent garments insulted with bodily wastes compared to absorbent garments that are not insulted with bodily wastes, the absorbent garments of the invention may have a saturated retention capacity of about 150 grams or greater.

In certain embodiments, the absorbent garment may have a waist elastic in the front waist region and/or in the back waist region with sufficient retraction force to maintain the garment in place on the wearer. In other embodiments, elastic components can be incorporated in the chassis components. For example, an elastic film can be incorporated in the chassis in such a manner that the elastic film provides sufficient retraction force to maintain the garment in place on the wearer. In still other embodiments, elastic components can be attached to the lateral edges of the back waist region and are referred to as elastic ears. As used herein, the term "waist elastic" may be used to describe any of the elastic elements in these embodiments, or a combination of the elements described in these embodiments. Suitably, the waist elastic may have a retraction force of about 100 grams or greater at 30% extension upon return after being extended at least 50%. Retraction force is measured as a sum of all of the waist elastic components located between the fastening components in the back waist region in the combined state in the diaper.

With the foregoing in mind, it is a feature and advantage of the invention to provide an absorbent garment having proportioned dimensions that result in a reduction or elimination of drooping or sagging in the crotch region.

BRIEF DESCRIPTION OF THE DRAWINGS

These and other objects and features of this invention will be better understood from the following detailed description taken in conjunction with the drawings, wherein.

DEFINITIONS

Within the context of this specification, each term or phrase below will include the following meaning or meanings.

"Absorbent garment" includes personal care garments, medical garments, and the like. The term "disposable garment" includes garments that are typically disposed of after 1-5 uses. The term "personal care garment" includes diapers, diaper pants, training pants, swim wear, absorbent underpants, adult incontinence products, feminine hygiene products, and the like.

"Attached" refers to the joining, adhering, connecting, bonding, or the like, of at least two elements. Two elements will be considered to be attached together when they are attached directly to one another or indirectly to one another, such as when each is directly attached to intermediate elements.

"Layer" when used in the singular can have the dual meaning of a single element or a plurality of elements.

Figure 3:
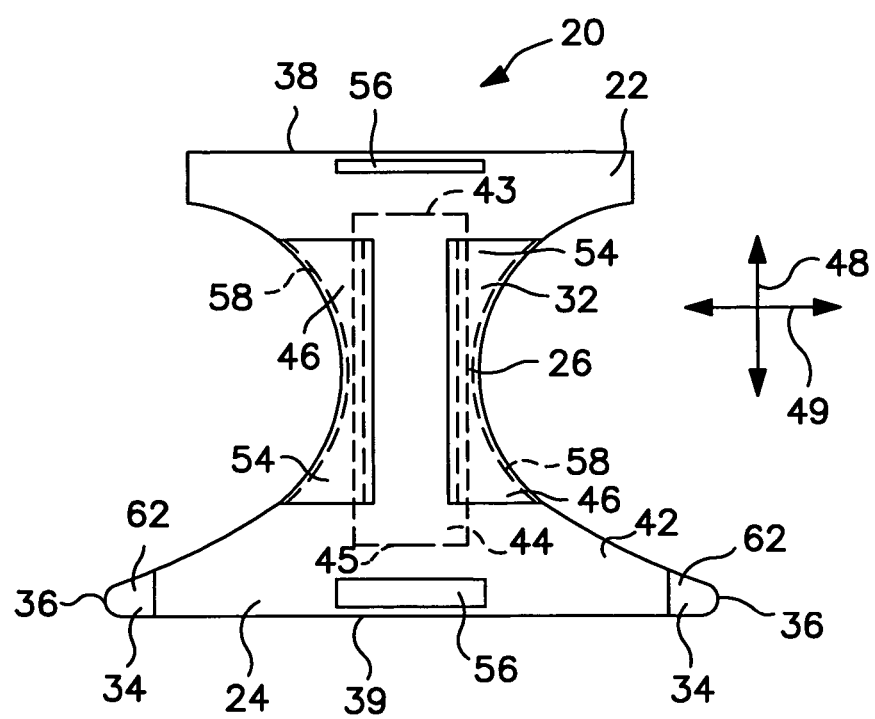
FIG. 3 is a plan view of the absorbent garment of FIG. 1 in a stretched flat state, and showing the surface of the garment that faces the wearer when the article is worn, according to one embodiment of this invention.

"Longitudinal" and "transverse" have their customary meaning, as indicated by the longitudinal and transverse axes depicted in FIG. 3. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such processes are known in the art. Meltblown fibers are microfibers which may be continuous or discontinuous, are generally smaller than about 0.6 denier, and are generally self bonding when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced, as known in the art. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent," "superabsorbent polymer," or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

These terms may be defined with additional language in the remaining portions of the specification.

Description of Preferred Embodiments

In accordance with the invention, an absorbent garment having dimensions of certain proportions results in a reduction or elimination of drooping or sagging in a crotch region. More particularly, dimensional proportions may be drawn between a longitudinal length of the absorbent chassis, an extended width of a back waist region of the garment, a width of a crotch region of the garment, and/or a longitudinal length of an absorbent core within the garment.

The principles of the present invention can be incorporated into any suitable pant-like disposable absorbent garment. Examples of such suitable garments include diapers, diaper pants, training pants, incontinence products, other personal care or health care garments, including medical garments, or the like. For ease of explanation, the description hereafter will be in terms of a diaper.

Figure 1:
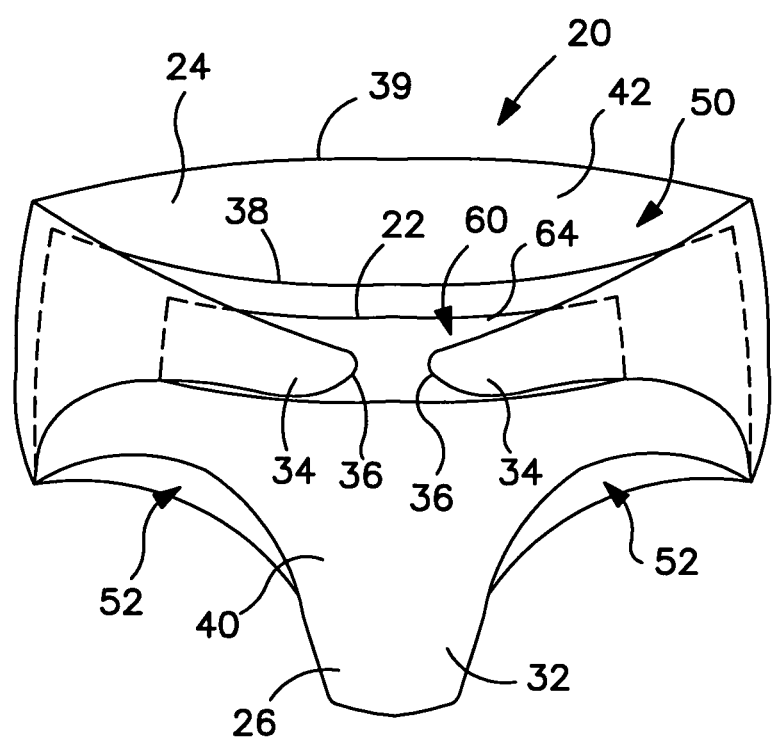
FIG. 1 is a perspective view of an absorbent garment, such as a diaper, having the proportional dimensions of the invention.
Figure 2:
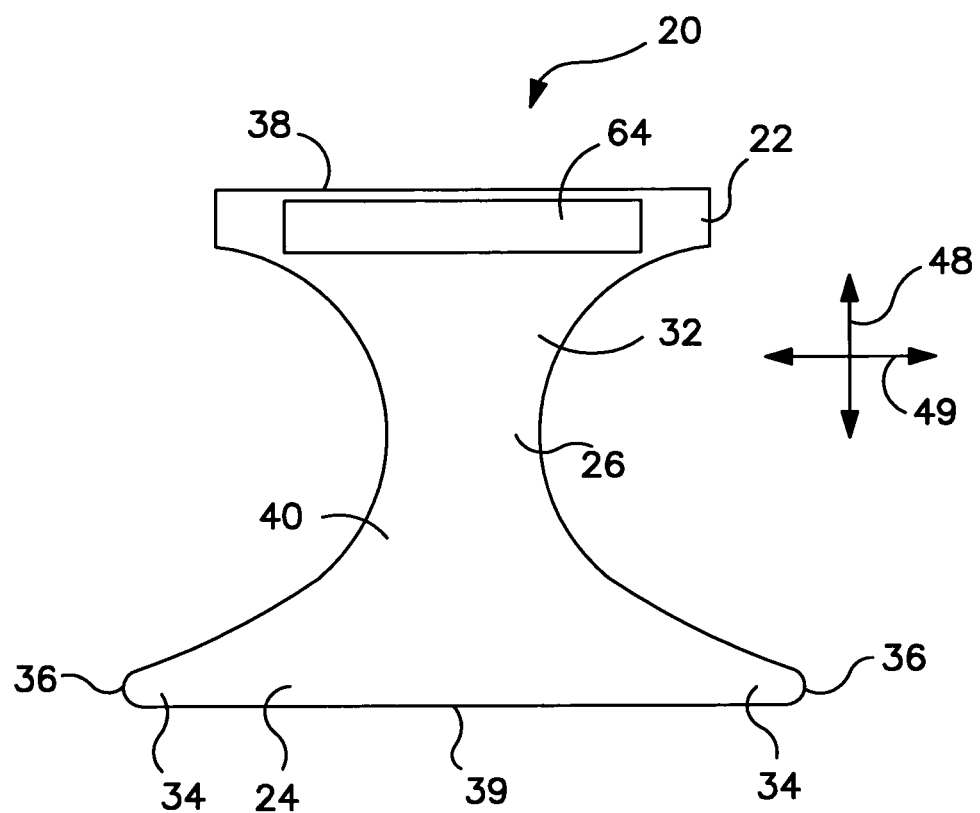
FIG. 2 is a plan view of the absorbent garment of FIG. 1 in a stretched flat state, and showing the surface of the garment that faces away from the wearer when the garment is worn, according to one embodiment of this invention.

Referring to FIG. 1, a diaper 20 is illustrated in a fastened position as the garment would appear when worn. FIGS. 2 and 3 illustrate the diaper 20 in a stretched flat state in which the various dimensions of the garment are measured. More particularly, FIG. 2 is a view of a garment-facing surface of the diaper 20, and FIG. 3 is a view of a body-facing surface of the diaper 20. The diaper 20 includes an absorbent chassis 32 defining a front waist region 22, a back waist region 24, and a crotch region 26 interconnecting the front and back waist regions. In the fastened position, the absorbent chassis 32 defines a three-dimensional pant configuration having a waist opening 50 and a pair of leg openings 52. The chassis 32 includes a body side liner 42 which is configured to contact the wearer, and an outer cover 40 opposite the body side liner which is configured to contact the wearer's clothing. An absorbent core 44 (FIG. 3) is positioned or located between the outer cover 40 and the body side liner 42.

The front waist region 22 includes the portion of the diaper 20 which, when worn, is positioned on the front of the wearer while the back waist region 24 includes the portion of the diaper which, when worn, is positioned on the back of the wearer. The crotch region 26 of the diaper 20 includes the portion of the diaper which, when worn, is positioned between the legs of the wearer and covers the lower torso of the wearer.

As shown in further detail in FIGS. 2 and 3, the chassis 32 also defines a pair of longitudinally opposed waist edges, which are designated front waist edge 38 and back waist edge 39. The front waist region 22 is contiguous with the front waist edge 38, and the back waist region 24 is contiguous with the back waist edge 39. The waist edges 38, 39 are configured to encircle the waist of the wearer when the garment is worn. A longitudinal length of the absorbent chassis 32 is the distance between the front waist edge 38 and the back waist edge 39, which can be measured according to the test method described in detail below. In the garment 20 of the invention, the longitudinal length of the absorbent chassis 32 is short compared to conventional garments designed to fit wearers of the same size. More particularly, the garments of the invention fit lower on a wearer, thereby using the small of the wearer's back to support the weight of the diaper. Consequently, less drooping occurs than with conventional diapers. For reference, arrows 48 and 49 depicting the orientation of the longitudinal axis and the transverse axis, respectively, of the diaper 20 are illustrated in FIGS. 2 and 3.

The illustrated absorbent chassis 32 includes a pair of transversely opposed ear panels or tabs 34, which extend transversely outward along the back waist region 24 of the absorbent chassis 32. The tabs 34 may be integrally formed with the outer cover 40 and/or the body side liner 42, or may include two or more separate elements. Additionally, the tabs 34 may include a stretchable and/or elastomeric material capable of stretching in a direction generally parallel to the transverse axis 49 of the diaper 20. Additionally, one or more of the chassis materials may be composed of an elastic material, in which case the addition of elastic strands or other elastic materials may not be necessary to deliver the required retraction force. An expanded width of the absorbent chassis 32 can be measured in a manner similar to the longitudinal length measurement test method described below, but with the measurements made from a distal edge 36 of one tab 34 to a distal edge 36 of the other tab 34 while one of the tabs is attached to a stationary object and a 1500 gram weight is attached to the other tab and permitted to hang for 10 seconds.

The expanded width of the absorbent chassis 32 measured in this manner provides an indication of the size of the garment with respect to a size of an intended wearer. More particularly, the absorbent garment 20 of the invention has a reduced longitudinal length compared to conventional absorbent garments, but the expanded width of the absorbent chassis 32 has not been reduced in the absorbent garment 20 of the invention compared to conventional absorbent garments. Thus, the expanded width of the absorbent chassis 32 can be used as a general garment size indicator when comparing garments of this invention to conventional absorbent garments to ensure that the garments being compared are intended to fit wearers of approximately the same size.

A width of the crotch region 26 may be narrower in the diaper 20 compared to conventional absorbent garments, as explained below in proportion to other dimensions of the diaper 20. The width of the crotch region 26 is measured across the narrowest transverse width of the crotch region 26 when the diaper 20 is in a laid flat state with any elastic components either removed or otherwise disabled to prevent any interference with the crotch width measurement, similar to the longitudinal length measurement test method described below.

The absorbent core 44 can be any structure which is generally compressible, conformable, non-irritating to the wearer's skin, and capable of absorbing and retaining liquids and certain body wastes at anticipated levels despite the narrowed crotch width. The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent core 44 to better contain and absorb body exudates. The absorbent core 44 can have variable thickness, with greater thickness in "target" areas, such as in a central portion of the crotch region. The concentration of the superabsorbent particles can also vary through the thickness of the absorbent core 44. Alternatively, the absorbent core 44 can include a laminate of fibrous webs and superabsorbent material or other suitable means of maintaining a superabsorbent material in a localized area. The absorbent core 44 may or may not be wrapped or encompassed by a suitable tissue wrap that maintains the integrity and/or shape of the absorbent core 44. In certain embodiments, the absorbent core 44 may contain a body side liner and/or a moisture barrier in addition to absorbent and distribution elements. In such embodiments, the absorbent core 44 may be attached to the outer cover 40 and need not be sandwiched between two layers. The absorbent core 44 may also contain leg elastics in embodiments such as this. The longitudinal length of the absorbent core 44 is measured from a front edge 43 of the absorbent core to a back edge 45 of the absorbent core in a laid flat position, negating any elastomeric effects from other components in the diaper 20.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Degussa Superabsorber in Greensboro, N.C., U.S.A. Typically, a superabsorbent material is capable of absorbing at least about 15 times its weight in water, and desirably is capable of absorbing more than about 25 times its weight in water.

The absorbent core 44 has a shorter length and width than the outer cover 40 and body side liner 42 and is spaced inboard from both the lateral side edges and the end edges of the outer cover and body side liner. The longitudinal length of the absorbent core 44 is measured in essentially the same manner as the longitudinal length of the absorbent chassis 32 as a whole, as described in the longitudinal length measurement test method described below.

The absorbent chassis 32 can also incorporate other materials that are designed primarily to receive, temporarily store, and/or transport liquid along the mutually facing surface with the absorbent core 44, thereby maximizing the overall absorbent capacity of the absorbent core 44, if desired. One suitable material is referred to as a surge layer (not shown), which may be positioned between the absorbent core 44 and the body side liner 42 to manage incoming fluid. Additionally, a vapor-permeable, hydrophobic spacer layer (not shown) may be positioned between the absorbent core 44 and the outer cover 40 as a further measure to prevent a clammy feeling on an outer surface of the outer cover 40 when the garment is loaded.

In at least one embodiment, the garment 20 with the absorbent chassis 32 has a saturated retention capacity of about 150 grams or greater, or about 250 grams or greater, or about 350 grams or greater, or about 450 grams or greater, or about 550 grams or greater. In certain embodiments, the saturated retention capacity of the garment 20 may be less than about 1500 grams. In certain embodiments, the saturated retention capacity of the garment 20 may be between about 250 grams and about 1000 grams. A test procedure for determining the saturated retention capacity is described in detail below.

The garment 20 of the invention has been configured in a manner that reduces or eliminates drooping or sagging in the crotch region 26 by reducing the longitudinal length of the absorbent chassis 32 and, optionally, reducing the width of the crotch region 26. More specifically, the garment 20 of the invention has a longitudinal length of the absorbent chassis 32 that is proportional to one or more other dimensions of the absorbent chassis 32 in a manner that does not hold true for currently available commercial diapers.

In at least one embodiment, the absorbent garment 20 has a relatively low diaper length ratio (DLR). The DLR is the longitudinal length of the absorbent chassis 32 divided by the expanded width of the absorbent chassis measured between the distal edges 36 of the tabs 34. The DLR is an indication of the length of the garment in proportion to the overall size of the garment, with a lower DLR indicating a shorter length. Suitably, the DLR is about 0.85 or less, or about 0.8 or less, or between about 0.6 and about 0.8.

In at least another embodiment, the absorbent garment 20 has a relatively low droop design ratio (DDR). The DDR is the longitudinal length of the absorbent chassis 32 multiplied by the width of the crotch region 26 and divided by the expanded width of the absorbent chassis measured between the distal edges 36 of the tabs 34. Thus, the DDR is the same as the DLR multiplied by the width of the crotch region 26. The DDR is an indication of both the length of the garment and the width of the crotch region in proportion to the overall size of the garment, with a lower DDR indicating a shorter length and/or a narrower crotch region. Suitably, the DDR is about 150 mm or less, or about 145 mm or less, or about 140 mm or less, or about 135 mm or less, or about 130 mm or less, or more than about 100 mm, or between about 120 mm and about 140 mm.

In at least one other embodiment, the absorbent garment 20 has a relatively low absorbent length design ratio (ALR). The ALR is the sum of the longitudinal length of the absorbent chassis 32 and the longitudinal length of the absorbent core 44, multiplied by the width of the crotch region 26 and divided by the expanded width of the absorbent chassis measured between the distal edges 36 of the tabs 34. Although similar to the DDR, the ALR differs from the DDR by accounting for the sum of the length of the absorbent chassis and the length of the absorbent core as a single length factor in the ratio. Thus, a lower ALR indicates a shorter total length of the garment plus the absorbent core and/or a narrower crotch region. With the reduction in absorbent garment droop, the length of the absorbent core 44 does not have to be as long to deliver protection since the absorbent core fits higher up on the body when droop is absent. Suitably, the ALR is about 280 mm or less, or about 275 mm or less, or about 270 mm or less, or about 260 mm or less, or about 250 mm or less, or about 240 mm or less, or between about 220 mm and about 250 mm.

The absorbent garment of the invention may include one or more of the embodiments described herein. The Example below compares the dimensions of commercially available diapers with two samples of absorbent garments of the invention.

In yet another embodiment, the absorbent garment 20 includes a waist elastic member 56 in the front waist region 22, in the back waist region 24, or in both the front and back waist regions 22, 24 of the garment, operatively joined to the outer cover 40 and/or body side liner 42 and extending across part or a full length of the waist edges 38, 39. Waist elastic members are often included in absorbent garments, but because of poor retraction strength, the waist elastic members may fail to maintain the garment at the wearer's waistline. In order to prevent the garment 20 from sliding down a wearer's body, and consequently causing the crotch region 26 to droop, the waist elastic member 56 suitably has a retraction force of about 100 grams or greater, or about 150 grams or greater, or about 200 grams or greater, or about 250 grams or greater, or about 300 grams or greater, or less than about 1500 grams, or between about 200 and about 600 grams, when measured at 30% extension upon return from an extension of at least 50%. The test procedure for measuring retraction force is ASTM D2433 with minor modifications listed below.

To further enhance containment and/or absorption of body exudates, the diaper 20 may include also leg elastic members 58, as are known to those skilled in the art (FIG. 3). The leg elastic members 58 may be operatively joined to the outer cover 40 and/or body side liner 42 along opposite side edges of the absorbent chassis 32 and positioned in the crotch region 26 of the diaper 20.

The waist elastic members 56 and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 56 may include a polystyrene-polyethylene-polypropylene-polystyrene (SEPS) block copolymer, such as KRATON® G2760, available from Kraton Inc. of Houston, Tex., U.S.A.

The diaper 20 may be refastenable, thereby including a refastenable fastening system 60 (FIG. 1) for securing the diaper about the waist of the wearer. One example of a suitable refastenable fastening system 60 may include fastening components 62, such as hook components, located along or adjacent to the distal edges 36 of the tabs 34. Suitable single-sided hook materials are available from Velcro Industries B.V., Amsterdam, Netherlands, or affiliates thereof. The fastening components 62 are adapted to refastenably connect to mating fastening components 64, such as loop material, located on an outer surface of the front waist region 22. One example of suitable loop material is "point unbonded" material. Point unbonded materials are fabrics having continuous thermally bonded areas defining a plurality of discrete unbonded areas and are described in greater detail in U.S. Pat. No. 5,858,515 issued Jan. 12, 1999 to Stokes, et al., incorporated herein by reference. The engaging elements of the fastening components 62 are adapted to repeatedly engage and disengage the engaging elements of the mating fastening components 64. With a relatively narrow crotch region 26 and a relatively short longitudinal length absorbent chassis 32, a single-point fastening system 60 is capable of maintaining a remarkable leg/hip fit to keep the diaper 20 suspended on the wearer even under extreme loads.

Additionally, the diaper 20 may include a pre-fastened, non-refastenable fastening system (not shown) to assist in applying the diaper 20 to a wearer. The non-refastenable fastening system may be torn when removing the diaper 20 from the wearer. The non-refastenable fastening system may be formed by attaching one edge of a loop material to a distal edge of the front waist region 22 of the absorbent chassis 32 and attaching an opposite edge of the same material to the tab 34 on the same side in the back waist region 24 of the garment with releasable bonds. Alternatively, the loop material may extend across a full width of the front waist region 22 of the absorbent chassis 32, thereby providing a mating fastening component 64, or landing strip, for the fastening components 62 of the refastenable fastening system 60, and extend even farther past the distal edges of the front waist region 22, such that the non-refastenable fastening system can be formed from the loop material that extends past the distal edges of the front waist region.

The outer cover 40 desirably includes a material that may be substantially liquid impermeable or liquid permeable, and can be elastic, stretchable, extensible, non-stretchable, or non-extensible. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer of the outer cover 40 desirably includes a material that can be elastic, stretchable, extensible, non-stretchable, or non-extensible. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain "non-breathable" elastic films can also be used to make the outer cover 40. Examples of suitable non-breathable films can be made of styrene-ethylene-butylene-styrene or styrene-isoprene-styrene block copolymers, KRATON® polymers from Kraton Inc. of Houston, Tex., U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent core 44, and may but need not have the same dimensions as the outer cover 40. The body side liner 42 is desirably compliant, soft feeling, and non-irritating to the wearer's skin. Further, the body side liner 42 can be less hydrophilic than the absorbent core 44, to present a relatively dry surface to the wearer and permit liquid to readily penetrate through its thickness. The body side liner 42 desirably includes a material that can be elastic, stretchable, extensible, non-stretchable, or non-extensible.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from available from Uniqema Inc., a division of ICI of New Castle, Del., U.S.A. and GLUCOPON® 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and body side liner 42 can include extendible and/or elastomeric materials, it can be desirable in some embodiments for the composite structure to be generally inelastic, where the outer cover, the body side liner and the absorbent core include materials that are generally not elastomeric.

To enhance containment and/or absorption of any body exudates discharged from the wearer, the chassis 32 may include a pair of containment flaps 46 which are configured to provide a barrier to the transverse flow of body exudates. A flap elastic member 54 (FIG. 3) may be operatively joined with each containment flap 46 in any suitable manner as is well known in the art. The elasticized containment flaps 46 define an unattached edge which assumes an upright, generally perpendicular configuration in at least the crotch region 26 of the diaper 20 to form a seal against the wearer's body. The containment flaps 46 can be located along the transversely opposed side edges of the chassis 32, and can extend longitudinally along the entire length of the chassis or may only extend partially along the length of the chassis. Suitable constructions and arrangements for the containment flaps 46 are generally well known to those skilled in the art.

As described herein, the various components of the absorbent garment 20 can be integrally assembled together employing various types of suitable attachment means, such as adhesive, sonic and thermal bonds or combinations thereof. The resulting product is a garment that has a reduced likelihood of drooping in the crotch region.

Test Methods

Longitudinal Length Measurement Test Method

The product (20) has an absorbent chassis length dimension measured between the front and back end edges (38 and 39) parallel to the longitudinal axis (48). The length dimensions of the product (20) are determined as follows.

A suitable method for determining the longitudinal length of the absorbent chassis (32) and the absorbent core (44) is to hang the product vertically adjacent a flat, smooth, vertical surface. One example of a suitable surface is a 0.25-inch thick acrylic plastic sheet available from Eagle Plastics and Supply of Appleton, Wis. Prior to hanging, the product is opened by opening any fasteners, cutting or opening any side seams, and unfolding any folded portions to make the absorbent garment flat, as shown in the plan views of FIGS. 2 and 3. Any elastic components that run the length of the chassis (such as leg elastics or elastics within containment flaps) are severed at least once per inch along their entire length. The product is hung with the back region (24) above the front region (22) and with the surface intended to face the wearer's outer garments during use positioned toward the flat, vertical surface. The top end margin of the product is held horizontal with two clamps, the inner edges of which are spaced 3.5 inches (8.9 cm) apart. The clamps are positioned adjacent the back waist edge 39 and, if possible, positioned to avoid any absorbent within the product, and are symmetrically disposed with respect to the longitudinal centerline/axis of the product. Any waist elastic present in the product is not stretched prior to securing the clamps.

The lower end of the hanging product (front waistband region) is clamped with a jig weighing 250 g. The jig possesses two clamp units (medium size, Bulldog clips, 2⅛ inch) attached to a tie rod (0.25-inch-20×12 inches, coarse thread, zinc plated), the clamps symmetrically placed with respect to the longitudinal centerline of the product, with a spacing between internal edges of the clamps of 3.5 inches (8.9 cm), with a 0.25-inch nut placed at the inner and outer edges of each clamp to hold the clamps in place. One (capped) bottle (1-ounce plastic screw cap bottle, such as NALGENE brand) is attached to each clamp with a piece of string. The assembly is placed on a laboratory balance and lead shot (No. 5 chilled lead shot, such as LAWRENCE brand) is added to each bottle (in equal amounts) until the total weight of the jig is as close to 250 grams as possible. The jig is attached to the lower end of the hanging product adjacent the front waist edge 38, as mentioned above.

For a typical product, a load of 250 g is appropriate. The elongate length of the absorbent chassis 32 is then determined by measuring the distance between the front and back end edges (38 and 39) along the longitudinal centerline/axis (48), between the clamps. The elongate length of the absorbent core 44 is then determined by measuring the distance between the front and back edges (43 and 45) along the longitudinal centerline/axis (48). Five specimens of each code are analyzed, and the results for each code are averaged.

Saturated Retention Capacity of Absorbent Articles

The saturated retention capacity is a measure of the total absorbent capacity of the absorbent article. The saturated retention capacity is determined as follows. The absorbent garment to be tested, having a moisture content of less than about 7 weight percent, is weighed and then submerged in an excess quantity of room temperature (about 23 degrees Celsius) saline solution, described below. The garment is allowed to remain submerged for 20 minutes. After 20 minutes, the absorbent garment is removed from the saline solution and placed on a TEFLON® coated fiberglass screen having 0.25-inch openings (commercially available from Taconic Plastic Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The absorbent garment is weighed again. The amount of aqueous liquid retained by the absorbent garment is determined by subtracting the dry weight of the absorbent garment from the wet weight of the absorbent garment (after application of the vacuum) and is reported as the saturated retention capacity in grams of aqueous liquid retained.

The saline solution is an aqueous solution of about 0.9 percent sodium chloride by weight. A suitable product is S/P® certified blood saline, commercially available from Baxter Diagnostics in Deerfield, Ill.

Retraction Force Test Method

The test procedure for retraction force is ASTM D2433. Differences from this test procedure for testing waist retraction include:

1. Testing the entire product by placing the fasteners in the jaws of a Sintech 500/S, available from MTS Systems Corp. of Eden Prairie, Minn., U.S.A., such that the clamped product delivers a force of about 10 grams plus the weight of the product.
2. Cycling the sample to 50% extension twice.

3. Measuring force in grams after the second extension to 50% and a return to 30% extension.

EXAMPLE

In this example, ten different diapers were measured and the proportions of these measurements were calculated in accordance with the proportions of the invention. Descriptions of the tested garments are provided in Table 1 below. Samples A and B (Garments 8 and 9) are garments of the invention. Samples A and B were constructed of the same materials as found in a HUGGIES® Convertibles, Step 5, available from Kimberly-Clark Corporation of Neenah, Wis., also used as Garment Number 4, and differ only in terms of dimensions, as listed in Table 2 below. More particularly, the dimensions of each of the tested diapers are presented in Table 2.

TABLE 1

Diapers Tested

| Garment Number | Description |
|---|---|
| 1 | PAMPERS ® Custom Fit Step 4 |
| 2 | PAMPERS ® Baby Dry Step 4 |
| 3 | HUGGIES ® Supreme Step 4 |
| 4 | HUGGIES ® Convertibles Step 5 |
| 5 | HUGGIES ® Ultratrim Step 4 |
| 6 | HUGGIES ® Ultratrim Step 2 |
| 7 | HUGGIES ® Ultratrim Step 6 |
| 8* | Sample A Step 4 |
| 9* | Sample B Step 4 |
| 10 | White Cloud Step 4 |

Note:
*An example of this invention

TABLE 2

Diaper Dimensions

| Garment | Length (mm) | Tab-to-Tab Width (mm) | Crotch Width (mm) | Absorbent Length (mm) | Retracted Length (mm) |
|---|---|---|---|---|---|
| 1 | 494 | 523 | 197 | 437 | 369 |
| 2 | 484 | 436 | 200 | 426 | 352 |
| 3 | 469 | 526 | 190 | 377 | 358 |
| 4 | 503 | 560 | 179 | 420 | 367 |
| 5 | 492 | 465 | 213 | 402 | 399 |
| 6 | 402 | 445 | 190 | 331 | 336 |
| 7 | 527 | 492 | 224 | 438 | 441 |
| 8* | 393 | 550 | 178 | 314 | 290 |
| 9* | 404 | 540 | 179 | 342 | 294 |
| 10 | 475 | 453 | 205 | 384 | 380 |

Note:
*An example of this invention

The dimensions listed in Table 2 were used to calculate the proportions presented in Table 3. The proportions in Table 3 include the DLR, the DDR, and the ALR, as described in detail above, along with the ratio of retracted length of the absorbent chassis to extended width of the chassis as measured from tab-to-tab, and the ratio of the crotch width of the absorbent chassis to extended width of the chassis as measured from tab-to-tab. Garments 8 and 9 are the only two garments that fall within the scope of the invention. The reacted length of the garment is measured from the same points as the longitudinal length of the absorbent chassis, but with the elastic materials, such as the leg elastics, in a completely retracted state. The ratio of retracted length to extended width further illustrates the short length of the garment of the invention even when in a relaxed state. The ratio of crotch width to extended width further illustrates the narrowness of the crotch with respect to the overall size of the garment.

TABLE 3

Diaper Proportions

| Garment | DLR | DDR | ALR | Retracted Length/Extended Width | Crotch Width/Extended Width |
|---|---|---|---|---|---|
| 1 | 0.94 | 186.27 | 351.15 | 0.71 | 0.38 |
| 2 | 1.11 | 222.39 | 418.13 | 0.81 | 0.46 |
| 3 | 0.89 | 168.99 | 304.93 | 0.68 | 0.36 |
| 4 | 0.90 | 161.08 | 295.69 | 0.65 | 0.32 |
| 5 | 1.06 | 225.02 | 409.02 | 0.86 | 0.46 |
| 6 | 0.90 | 171.78 | 313.11 | 0.75 | 0.43 |
| 7 | 1.07 | 240.29 | 440.00 | 0.90 | 0.46 |
| 8* | 0.71 | 126.84 | 228.38 | 0.53 | 0.32 |
| 9* | 0.75 | 133.92 | 247.17 | 0.55 | 0.33 |
| 10 | 1.05 | 215.46 | 389.36 | 0.84 | 0.45 |

Note:
*An example of this invention

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent garment, comprising:
an absorbent chassis defining a waist opening and first and second leg openings, wherein when in a flat state the absorbent chassis includes opposing curved side edges extending from a back waist region;
the absorbent chassis having a longitudinal length, wherein the longitudinal length is determined by severing elastic components, in at least a single location, that run the length of the absorbent chassis and suspending the garment with a weight attached thereto, and first and second tabs defining transverse distal edges of the back waist region of the absorbent chassis; and
the absorbent chassis having a diaper length ratio of about 0.85 or less, wherein the diaper length ratio is the longitudinal length of the absorbent chassis divided by an expanded width of the absorbent chassis measured from a distal edge of the first tab to a distal edge of the second tab.

2. The absorbent garment of claim 1, wherein the diaper length ratio is about 0.8 or less.

3. The absorbent garment of claim 1, wherein the diaper length ratio is between about 0.6 and about 0.8.

4. The absorbent garment of claim 1, further comprising a waist elastic in at least one of the front and back waist regions, wherein the waist elastic has a retraction force of about 100 grams or greater at 30% extension upon return from an extension of at least 50%.

5. The absorbent garment of claim 1, further comprising a waist elastic in at least one of the front and back waist regions, wherein the waist elastic has a retraction force between about 200 grams and about 600 grams at 30% extension upon return from an extension of at least 50%.

6. The absorbent garment of claim 1, wherein the absorbent chassis has a saturated retention capacity of about 150 grams or greater.

7. The absorbent garment of claim 1, wherein the absorbent chassis has a saturated retention capacity between about 250 grams and about 1000 grams.

8. The absorbent garment of claim 1, wherein the absorbent chassis comprises a crotch region positioned between front and back waist regions, and the absorbent chassis has a droop design ratio of about 150 millimeters or less, wherein the droop design ratio is the longitudinal length of the absorbent chassis multiplied by a width of the crotch region of the absorbent chassis and divided by the expanded width of the absorbent chassis measured from the distal edge of the first tab to the distal edge of the second tab.

9. The absorbent garment of claim 1, wherein the absorbent chassis comprises an outer cover, a body side liner, and an absorbent core positioned between the outer cover and the body side liner; and a crotch region positioned between front and back waist regions of the absorbent chassis; and the absorbent chassis has an absorbent length design ratio of about 280 millimeters or less, wherein the absorbent length design ratio is the sum of the longitudinal length of the absorbent chassis and a longitudinal length of the absorbent core, multiplied by a width of the crotch region of the absorbent chassis and divided by the expanded width of the absorbent chassis measured from the distal edge of the first tab to the distal edge of the second tab.

10. A diaper comprising the absorbent garment of claim 1.

11. An absorbent garment, comprising:

an absorbent chassis defining a waist opening and first and second leg openings;

the absorbent chassis having a longitudinal length, wherein the longitudinal length is determined by severing elastic components, in at least a single location, that run the length of the absorbent chassis and suspending the garment with a weight attached thereto, a crotch region positioned between front and back waist regions of the absorbent chassis, and first and second tabs defining transverse distal edges of the back waist region of the absorbent chassis; and the absorbent chassis having a droop design ratio of about 150 millimeters or less, wherein the droop design ratio is the longitudinal length of the absorbent chassis multiplied by a width of the crotch region of the absorbent chassis and divided by an expanded width of the absorbent chassis measured from a distal edge of the first tab to a distal edge of the second tab.

12. The absorbent garment of claim 11, wherein the droop design ratio is between about 120 and about 140 millimeters.

13. The absorbent garment of claim 11, further comprising a waist elastic in at least one of the front and back waist regions, wherein the waist elastic has a retraction force of about 100 grams or greater at 30% extension upon return from an extension of at least 50%.

14. The absorbent garment of claim 11, further comprising a waist elastic in at least one of the front and back waist regions, wherein the waist elastic has a retraction force between about 200 grams and about 600 grams at 30% extension upon return from an extension of at least 50%.

15. The absorbent garment of claim 11, wherein the absorbent chassis has a saturated retention capacity of about 150 grams or greater.

16. The absorbent garment of claim 11, wherein the absorbent chassis has a saturated retention capacity between about 250 grams and about 1000 grams.

17. The absorbent garment of claim 11, wherein the absorbent chassis comprises an outer cover, a body side liner, and an absorbent core positioned between the outer cover and the body side liner; and the absorbent chassis has an absorbent length design ratio of about 280 millimeters or less, wherein the absorbent length design ratio is the sum of the longitudinal length of the absorbent chassis and a longitudinal length of the absorbent core, multiplied by the width of the crotch region of the absorbent chassis and divided by the expanded width of the absorbent chassis measured from the distal edge of the first tab to the distal edge of the second tab.

18. A diaper comprising the absorbent garment of claim 11.

19. An absorbent garment, comprising:

an absorbent chassis comprising an outer cover, a body side liner, and an absorbent core positioned between the outer cover and the body side liner, the absorbent core defining a waist opening and first and second leg openings;

the absorbent chassis having a longitudinal length, wherein the longitudinal length is determined by severing elastic components, in at least a single location, that run the length of the absorbent chassis and suspending the garment with a weight attached thereto, a crotch region positioned between front and back waist regions of the absorbent chassis, and first and second tabs defining transverse distal edges of the back waist region of the absorbent chassis; and the absorbent chassis having an absorbent length design ratio of about 280 millimeters or less, wherein the absorbent length design ratio is the sum of the longitudinal length of the absorbent chassis and a longitudinal length of the absorbent core, multiplied by a width of the crotch region of the absorbent chassis and divided by an expanded width of the absorbent chassis measured from a distal edge of the first tab to a distal edge of the second tab.

20. The absorbent garment of claim 19, wherein the absorbent length design ratio is between about 220 and about 250 millimeters.

21. The absorbent garment of claim 19, further comprising a waist elastic in at least one of the front and back waist regions, wherein the waist elastic has a retraction force of about 100 grams or greater at 30% extension upon return from an extension of at least 50%.

22. The absorbent garment of claim 19, further comprising a waist elastic in at least one of the front and back waist regions, wherein the waist elastic has a retraction force between about 200 grams and about 600 grams at 30% extension upon return from an extension of at least 50%.

23. The absorbent garment of claim 19, wherein the absorbent chassis has a saturated retention capacity of about 150 grams or greater.

24. The absorbent garment of claim 19, wherein the absorbent chassis has a saturated retention capacity between about 250 grams and about 1000 grams.

25. A diaper comprising the absorbent garment of claim 19.

* * * * *